US 6,481,648 B1
United States Patent
Zimmermann (10) Patent No.: US 6,481,648 B1
(45) Date of Patent: Nov. 19, 2002

(54) SPRAY TIP FOR A MICROFLUIDIC LABORATORY MICROCHIP

(75) Inventor: Hans-Peter Zimmermann, Karlsruhe (DE)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/570,947

(22) Filed: May 15, 2000

(30) Foreign Application Priority Data

Oct. 1, 1999 (DE) .......................................... 199 47 496

(51) Int. Cl.[7] .................................................. B05B 5/00
(52) U.S. Cl. ........................ 239/690; 239/589; 239/691; 239/692
(58) Field of Search ................................ 239/589, 690, 239/691, 692

(56) References Cited

U.S. PATENT DOCUMENTS

| | | | | |
|---|---|---|---|---|
| 6,042,709 A | * | 3/2000 | Parce et al. ................. | 204/450 |
| 6,086,740 A | * | 7/2000 | Kennedy .................... | 204/601 |
| 6,176,962 B1 | * | 1/2001 | Soane et al. ................ | 204/450 |
| 6,322,683 B1 | * | 11/2001 | Wolk et al. ................. | 204/601 |

FOREIGN PATENT DOCUMENTS

WO 97/04297 2/1997

OTHER PUBLICATIONS

A Van Den Berg and P. Bergveld, ed. Micro Total Analysis Systems. The Netherlands: Kluwer Academic Publishers, 1995. MESA Research Institute monographs, Contents overview.

* cited by examiner

*Primary Examiner*—Robin O. Evans (57) ABSTRACT

A laboratory microchip includes a carrier with a micro spray tip projecting vertically out of a plane of the carrier. The carrier and spray tip are designed as a monolithic or single unit. The spray tip includes a passage channel which conveys the substances to be sprayed from a channel to a spray tip aperture. The channel is a part of a channel structure which is enclosed to the outside by a cover plate. The spray tip includes, on the sides of the spray aperture, an area which tapers conically inwards. Connected to this tapered area is a constant cross-section drill hole forming an annular internal step formation at the transition between the two areas. The outer diameter of the conically tapering tip is locally reduced in proximity to the aperture to provide a finer tip to the spray tip. The finer tip increases the electrical fields occurring at the tip, to further increase the forces which act on the substances and for dispersion spraying.

23 Claims, 5 Drawing Sheets

SPRAY TIP FOR A MICROFLUIDIC LABORATORY MICROCHIP

The invention relates in general to microchip laboratory systems which serve to carry out chemical, chemical-physical, physical, biochemical and/or biological processes, in particular for the analysis or synthesis of substances on a carrier which features a microfluidic structure. The essentially flat carrier in this situation features a micro-channel structure, by means of which the substances are capable of movement in accordance with the channel structure under the imposition of a potential particularly an electrical potential. In particular, the invention relates to such microchip systems in which a micro spray tip is provided for spraying substances to the outside particularly for the insertion spraying of substances into a mass spectrometer. In addition, the invention relates to a process for the manufacture of a microchip featuring such a micro spray tip, as well as a device for handling such a microchip.

The rapid progress in the sector in question can best be illustrated by way of the corresponding developments in the microelectronics sector. In the chemical analysis sector, too, not least with regard to clinical outpatient diagnosis, there is a substantial demand for existing stationary laboratory equipment to be integrated into portable systems, or for such systems to be miniaturised accordingly. An overview of the latest developments in the sector of laboratory microchip technology can be found in a collection of pertinent specialist publications edited by A. van den Berg and P. Bergveld under the title "Micrototal Analysis Systems", published by Kiuwer, Academic Publishers, Netherlands, 1995. The starting point for these developments was the already established method of what is referred to as "capillary electrophoresis", with which efforts have already been made in the past to implement the system on a planary glass microstructure.

Figure 1:
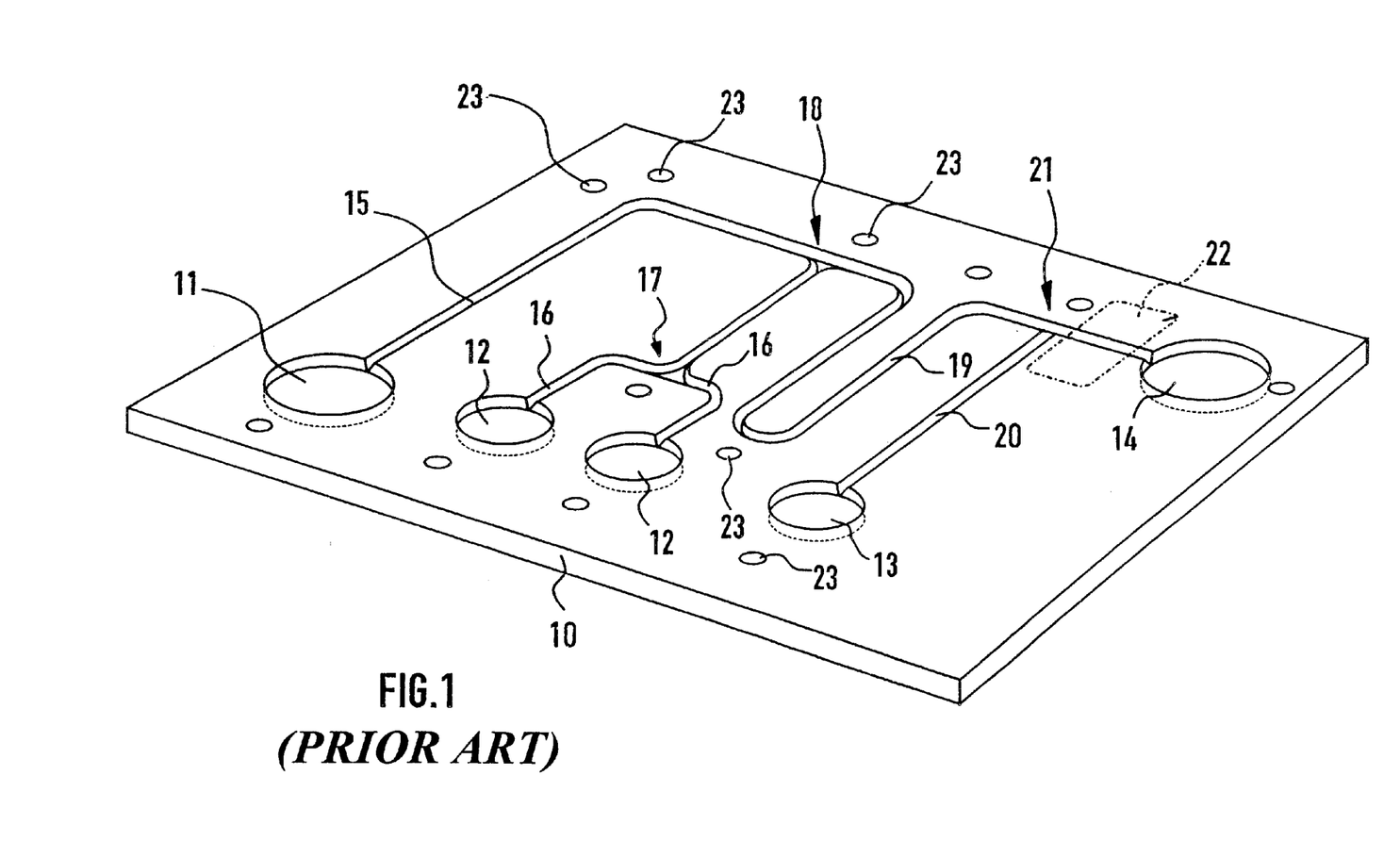
FIG. 1 a laboratory microchip according to the prior art.

FIG. 1 shows a conventional laboratory microchip. As shown on the upper surface of a substrate or carrier 10, microfluidic structures are applied, which serve to accommodate and transport substances. The carrier 10 may be made, for example, of glass or silicon, whereby the structures can be created by means of a chemical or laser-supported etching process. To accommodate a substance which is to be examined (referred to hereinafter as the "substance specimen") on the microchip, one or more indentations 11 are provided on the carrier, which serve as a reservoir for the individual substance specimen. For the purpose of conducting the experiment, the substance specimen is initially moved along a transport channel 15 on the microchip. In the present embodiment, the transport channel is formed by a V-shaped groove. There are, however, in principle other embodiments of the transport channel possible, such as rectangular or circular profiled cut-outs or grooves. Other depressions 12, serving likewise as substance reservoirs or wells, accommodate the reagents required for the performance of the experiment. In the present example, this involves two different substances, these being initially conducted by means of corresponding transport channels 16 to a point of intersection 17, where they intermix and, after chemical analysis or synthesis has been carried out if appropriate, they form the product which is ultimately to be used. At a further point of intersection 18, this reagent then encounters the substance specimen which is to be examined, whereby both substances are likewise intermixed.

The substance which is formed in this overall manner then runs through a meander-shaped transport section 19, which serves essentially to enlarge artificially the lengths of the distances available for the reaction between the substance specimen and the reagent. In the present example, in a further indentation 13, formed as a substance reservoir or well, an additional reagent is contained which is conducted to the substance mixture which already pertains, at a further point of intersection 21.

In the present example, the substance reaction which is actually to be examined takes place immediately adjacent to the point of intersection in reference 21. The detection of this substance reaction then takes place within a measurement field or area 22 of the transport channel by means of a detector, not shown here, for preference free of contact. An appropriate detector may in this case be arranged above or below the area 22. Once the substance has run through said area 22, it is conducted to a further indentation 14, which represents a substance sink for the substance waste residues formed overall during the reaction.

Finally, depressions 23 are provided on the microchip which function as contact surfaces for the application of electrodes, and which in turn allow for the imposition on the chip of the electrical voltages, and high voltages in particular, which are required for the operation of the chip. As an alternative, the contact for the microchip can also be provided by the introduction of an appropriate electrode to directly into the depressions 11, 12, 13, 14 provided for the accommodation of the substances. By means of a suitable arrangement of the electrodes 23 along the transport channels 15, 16, 19, 20 and a corresponding temporal and/or strength concordance of the fields used, a situation can now be attained in which the movement of the individual substances is effected in accordance with a temporal and volume profile which can be precisely predetermined, with the result that the kinetics of the reaction process taken as the basis in each case can be most precisely taken into consideration, and can be maintained respectively.

In the case of the movement of the substances by means of gas pressure (not shown here) within the microfluidic structure, it is necessary for the transport channels to be designed as conduits enclosed all round, for example as hollow channels with predetermined cross-sections. In such an embodiment, it is therefore necessary for the depressions 23 to be designed in such a way that suitable pressure supply lines engage in them, duly sealed, in order for a pressure medium, such as a noble gas, to be introduced into the transport channels.

Miniaturisation of the microchips also allows for a substantial shortening of the transport paths for the substances, especially between the introduction point for the substances and the individual detection point for the measurement of a chemical reaction which is to be effected (see FIG. 1). From the sector of liquid chromatography and electrophoresis the principle is further known of a substance separation being implemented more rapidly in such systems, and therefore of the results of experiments likewise being provided more rapidly, and for the individual components to be separated with higher resolution than is possible in conventional systems. In addition to this, microminiaturised laboratory systems also allow for a substantial reduction in the consumption of substances, in particular of reagents, as well as a substantially more efficient mixing of the substance components.

A laboratory microchip of the type shown in FIG. 1 has been described, for example, in U.S. Pat. No. 5,858,195. The movement of the substances in the channels integrated on the microchip is controlled by means of electric fields, which are imposed along the transport channels. Because of the highly precise control of the substance movement which is achieved by this, and the very precise metering ability of the substance masses moved in each case, the substances can be mixed or separated precisely in relation to the desired stoichiometry, or physical-chemical reactions can be induced. The movement of the substances is effected in this case on the basis of what is referred to as electro-osmosis; i.e. the movement of individual substances within a substance mixture incurred by an electrical potential gradient. Substances move in electrical fields on the one hand due to their space charge. The space charge can for example be controlled by an appropriate chemically acidic environment. This is referred to as the electrophoretic flow. At the same time, each surface has a surface charge. Formed directly on the inner surface of a capillary, as a result of this surface charge (mostly negative) is a thin layer of the corresponding counter-charge (mostly positive) in the mobile phase (liquid). In the electrical field this thin layer migrates backwards and forwards, and takes the liquid in the interior of the capillaries with it. This flow is referred to as the electro-osmotic flow (EOF). The total flow is the sum of the EOF and the electrophoretic flow, whereby neutral molecules migrate with the EOF.

In particular, the microchip described in the aforesaid US Patent features a carrier with one or more points of intersection between the transport channels, at which intermixing of substances takes place. By the simultaneous application of different electrical potentials at different substance reservoirs or wells, the possibility is provided of the volume flows of the different substances being selectively controlled through one or more points of intersection, and therefore of a precise stoichiometric predetermination being rendered possible solely on the basis of the electrical potentials applied.

To detect the substance reactions taking place during an experimental procedure, optical procedures are mainly used, e.g. by the measurement of an absorption spectrum or fluorescence spectrum of the individual substance in each case. Optical detection in this situation requires transparent materials within the channel structure of such a microchip, such as glass or polymethyl metacrylate (PMMA). At the same time, it is necessary for the substance specimen which is to be detected to be marked in an absorbent manner either in the area of the individual wavelength of the measuring beam, or appropriately marked with fluorescing colouring agents. The restrictions which this induces in the selection of the substance specimens imply considerable disadvantages for such microfluidic measuring devices.

In addition to this, in many applications, such as in the field of protein analytics, optical detection is often difficult or can only be effected with considerable technical effort. In the prior art it was therefore proposed that a mass spectrometer (MS) be connected to a microfluidic microchip of the type described in the preamble. Usually an arrangement referred to as an "electrospray interface" (ESI) is used in this situation, in order for the liquid substance specimens present for the MS detection to be ionised beforehand. "Electrospray" ionisation serves in this case to generate ions for the mass-spectroscopic analysis of chemical or biological substance specimens. An ESI pertains when a liquid in a capillary tip (spray tip) is subjected to an electrical potential of a value of some 1–4 kV (kiloVolt). The high electrical field induces charges on the surface of the liquid in the area of the spray tip. The spraying off or dispersant spraying of the substance in the area of the spray tip occurs as soon as the Coulcombe forces are great enough to overcome the surface tension forces present in the liquid. Ionisation by means of an ESI for flow rates such as typically arise in microfluidic structures (100–500 nl/min) do however require very high electrical field strengths, such as can only be created with very fine spray tips with a diameter of about 10–100 μm (micrometres).

Pertinent microfluidic systems of the type in question have been disclosed, for example, in the patent specifications WO 97/04297, WO 98/35376, and U.S. Pat. No. 5,788,166. The microfluidic system disclosed in WO 97/04297 features a micro spray tip which serves as an "ESI" interface for the transfer of substance specimens to a mass spectrometer. In an embodiment of the type disclosed there, the spray tip is manufactured in a construction unit with one or more channels. In addition, the spray tip projects, in relation to the surface plane of the microchip carrier, vertically out of this plane, whereby the tip according to FIG. 2b is likewise manufactured in a construction unit with a cover plate. The actual channel system is created on the side of the carrier turned away from the spray tip, by the provision of an appropriately dimensioned cover plate.

In the printed specification referred to, a spray tip is described which is micro-mechanically manufactured from silicon. This spray tip is in this case formed from a supporting substrate, for preference a silicon carrier. The liquid substance specimen in this situation flows first into a channel structure as previously described. At one end of this channel structure a spray tip is created, in the form of a channel, which is in a substance conductive connection with the channel structure. The manufacture of the spray tip is effected by means of numerous manufacturing stages, whereby multi-stage depositing processes are encompassed to form what is referred to as a "sandwich". This sandwich features on the outer sides two silicon-nitrite layers in each case. The spray tip itself is formed in this case by means of an etching process. The silicon-nitrite layers in this case are initially deposited on a silicon substrate. Thereafter the silicon-nitrite is structured by means of a plasma, with the formation of the spray tip.

The ESI source described in U.S. Pat. No. 5,788,166 also features a micro spray tip of the type described in the preamble, and is particularly well-suited for the atomization of liquid substances for use in the sector of capillary electrophoresis with ultra-low flow rates. The spray tip is created by tensile extension (drawing out) of a heated quartz tube. The quartz tube in this case is processed by chemical etching and subsequent surface metal coating subsequent to the tensile extension. The extension of the tube leads in particular to the formation of a channel or capillary, slowly tapering to a point, located within a needle-shaped extension, which, in addition, runs into a tip with an extremely small internal diameter. The etching process leads to a further thinning of the outer wall of the needle, and therefore to a further reduction of the diameter of the tip. After the application of a metallised electrical contact on the outer wall of the needle, an electrically insulating cover layer is then applied, which contributes towards increasing the service life of the needle.

A spray tip drawn out of a glass capillary is also described in Anal. Chem. 98, 70, 3728–3734, whereby the glass capillary is adhesively bonded into a microchip after being drawn out. The electrical connection in this case is created either via a metallized tip or by means of what is referred to as a "liquid junction" on the chip. A liquid junction of this type, as an electrical connection for the ESI is also described in Anal. Chem. 97/69, 1174–1178. Instead of a spray tip, however, in this case what is referred to as a spray cone (Tayler Cone) is provided directly on the surface of a microchip. The liquid junction in this case is formed as an additional channel shortly before the spray cone. In order to prevent the possibility of the specimen molecules not following the electrical field along these connection channels, the connection channel is coated in such a way that no field edge pertains within the connection channel which would cause an electro-osmotic flow (EOF) of the substances.

The generation of such micro-tips can also be effected in a known manner by lithographic deposit processes, for example by the formation of parallels on the surface of a microstructure, making use of what is referred to as a sacrificial layer, which is subsequently dissolved, and so forms a channel. As in the process proposed in WO 98/35376, the individual manufacturing stages in this case are:

1. Layer of silicon nitrite on silicon (as base)
2. Phosphosilicate glass (as sacrificial layer)
3. Layer of silicon-nitrite (as cover and side wall)
4. Free etching of the tip (silicon carrier is freely etched)
5. Sacrificial layer is etched away.

The principle is also known of manufacturing a micro-tip by deep etching or ionic etching of silicon structures in such a way that, after the etching, the micro-tip remains. Such a manufacturing process is disclosed, for example, in a contribution by R. E. Swenson at an IBC Conference held on Sep. 9, 1999.

The microtips described heretofore now have the disadvantage that, because of the relatively elaborate manufacturing processes involved, there are at present no microstructure couplings of laboratory microchips of the previously described type, such as mass spectrometers or the like, which are capable of commercialisation.

The object underlying the invention is therefore to provide a microchip which features a micro spray tip of the type described in the preamble, the manufacture of which is simplified in comparison with the prior art. The microstructure to be created in this situation is intended, in addition to simplified means of manufacture, in particular to allow for the most reliable means of manufacture of extremely fine spray tips with an outer diameter of 10–100 $\mu$m (micrometres). A spray tip of this kind should also provide a hydraulic connection, created in the simplest manner possible, to the separation channel system provided in each case on the microchip, as well as a simplified electrical connection for the electrical field required for the dispersion spraying of the substances from the spray tip.

The object underlying the invention is also to provide a device for the handling of a laboratory microchip featuring a micro spray tip, which will facilitate or render easy the use of such a microchip, in particular the coupling of the microchip to a mass spectrometer.

The objects indicated are achieved according to the invention by the features of the independent claims. Preferred and advantageous embodiments of the invention are described in the dependent claims.

The special feature of the present invention in comparison with the prior art described in the preamble lies in the fact that the micro spray tip is prepared from a carrier material in such a way that the spray tip and the carrier are formed in a single piece, in particular in a monolithic manner. In addition to this, the channel structure provided on the microchip is arranged in the side of the carrier which is backwards to the spray tip, and can be automatically connected in a substance-conductive manner by means of the manufacturing method to be described in detail hereinafter.

The advantages of the proposed arrangement of the micro tip and of the manufacturing process relating to this lie in particular in the fact that the manufacture of the spray tip is rendered substantially easier, and that therefore a reduction in costs can be achieved in the manufacture of these tips, which in overall terms makes the marketing of microchips featuring these spray tips possible as a mass article. The proposed microstructure can be manufactured to advantage by hot embossing or by micro injection moulding. By means of such or similar processes, the fine structures required, such as are necessary for an ESI, and in particular a truncated cone with a tip diameter of some 10–100 $\mu$m (micrometres) and a height of about 1 mm, can be manufactured to advantage.

By contrast with the prior art, in which at present the structuring of microchips is only possible on one side, the manufacturing process proposed according to the invention allows for an initial substrate to be structured on both sides; i.e. the formation on one side of the carrier of a channel structure with separation and delivery channels, and, at the same time, on the other side of the carrier the formation of a micro tip. The connection channel required between the channel structure and the spray tip can be created to advantage by laser drilling.

The channel structure can also be sealed or closed off to the outside by means of a cover plate, which is applied onto the carrier, following the manufacture of the micro tip. The connection channel between the channel structure and the spray tip can to advantage be formed as early as in the laser or injection mould, in particular in one work sequence with the manufacture of the micro tip and/or the channel structure. This allows the manufacturing costs to be further reduced.

In a further embodiment, an electrical connection is created for the spray tip by means of what is referred to as a "liquid junction". The electrical supply to the spray tip is effected to advantage in this case by means (via the connection channel) of the substances being fed to the spray tip. This embodiment accordingly does not require any additional electrical devices, for example in the form of a metallization layer or similar.

In order to prevent the possibility with the embodiment described of specimen molecules migrating into the connection channel (the channel for connecting the spray tip with the channel structure) instead of to the spray tip, it is to advantage for a pressure to be imposed at the connection channel of the liquid junction, increased by such a degree that the hydrodynamic flow created by this pressure is greater than or equal to the electro-osmotic flow (EOF). In addition to this, by specific adjustment of these pressure conditions, by the provision of an electrical connection for the spray tip, it is also possible in a specific manner for an additional liquid to be mixed into the substances which are to be examined, in order to optimise the ESI. For example, in this situation, organic acids may be added, such as formic acid or acetic acid, in order to improve the charging (proton building) of the substance specimen. As an alternative, or in addition, organic solvents such as methanol may be added, in order to optimise the spraying off or dispersion atomization.

The invention further relates to a device for handling a microchip according to the invention, in which provision is made for a flat formed carrier unit with hollow spaces arranged next to one another in the plane of the surface to accommodate the substances which are to be conducted to the microchip. The hollow spaces are in this case arranged in concordance with corresponding delivery apertures of the microchip in the said surface plane. In addition to this, the microchip can be connected to the carrier unit in a substance-conducting manner on the side which features the channel structure.

The proposed device accordingly allows for the use of standardised substance specimen holders (microtiter plates, known as "well plates"), such as are already available on the market in a large number of automation robots and pipetting stations. Typically, the specimen transfer is effected from a well plate to a microfluidic microchip by pipetting up the liquids in each case or by the use of what is referred to as a transfer capillary, which is adhesively bonded into the microchip.

In particular, the device allows for the handling of the specimen and the specimen analysis to be combined in one function module, so that the specimen does not need to be additionally transferred from a well plate to the microchip. According to a preferred embodiment of the invention, the microfluidic microchip is designed in this context as a base piece of a well plate.

In addition, the proposed handling device allows for simplified automation, in particular of microchips with integrated spray tips. It is further advantageous for the micro tip, which forms the interface to the mass spectrometer, to be arranged on the underside of the microfluidic chip, so that the spray tip sprays downwards.

A further advantage of the device lies in the fact that the microchip can now be provided in the same geometric format as the dimensions of the well plate used in each case. Accordingly, during the handling of the specimen or the organisation of the specimen there is no longer any need to distinguish between the specimens themselves and the microchips. By the use of a standard frame for the arrangement of the delivery channels for the substances, it is possible to make use of conventional commercial specimen preparation devices for the off-line operation of the substance preparation.

Provision can further be made, instead of the use of an individual microchip, for a well plate rack to be provided, on which several microchips can be secured.

According to a further advantageous embodiment of the concept according to the invention, the microchip is designed longitudinally in relation to the plane of the surface, so that at least two microchips of longitudinal design of this nature can be arranged longitudinally next to one another in the plane of the surface, capable of being connected to the well plate in a substance-conducting manner. With this embodiment of the microchip, it is further of advantage for a separation channel to be arranged orientated in the longitudinal direction of the microchip, for the separation (analysis) of substances, in order thereby to maximise the (effective) length of the separation channel, and nevertheless avoid an excessively complex and elaborate channel arrangement. An arrangement of several such longitudinal microchips on a well plate further has the advantage that several different experiments can be carried out simultaneously on one single well plate. Thanks to the reduced number of well plates per microchip required with this arrangement, manufacturing costs are reduced on the one hand, and the time of the measuring cycles is reduced on the other.

The manufacturing process likewise proposed according to the invention, for a micro tip in question, features the special characteristic that the connection channel between the channel structure and the micro tip can be manufactured by a process which contains only a few stages. It is indeed possible with the prior art, by hot embossing or micro tip casting, to create micro tips with a tip diameter of about 15 to 100 $\mu$m (micrometer), but with these small diameters it is not possible for the penetration aperture to be manufactured jointly (simultaneously) in one work stage, since the wall thickness would then only amount to a few micrometres. Accordingly, with the process according to the invention, a blind hole is first prepared by means of hot embossing, micro injection moulding, or an alternative manufacturing process is initially provided, of only about 30 $\mu$m (micrometres) in front of the penetration point of the drill hole at the micro tip, so that only a thin membrane remains. It is then possible, with the aid of a laser or similar device, for the blind hole to be opened towards the tip.

To advantage, it is possible, at the spray tip, if appropriate even in one manufacturing process with the manufacture of the spray tip, for preference by laser ablation, for material located on the aperture diameter of the tip to be removed in order thereby to reduce the diameter of the tip even further.

The invention is described hereinafter on the basis of embodiments, whereby other objects, advantages, and features of the invention are derived from this description alone or in connection with the patent claims.

The drawings show, individually:

FIG. 1 shows a laboratory microchip known from the prior art, which has already been described in detail in the Description preamble.

Figure 2A:
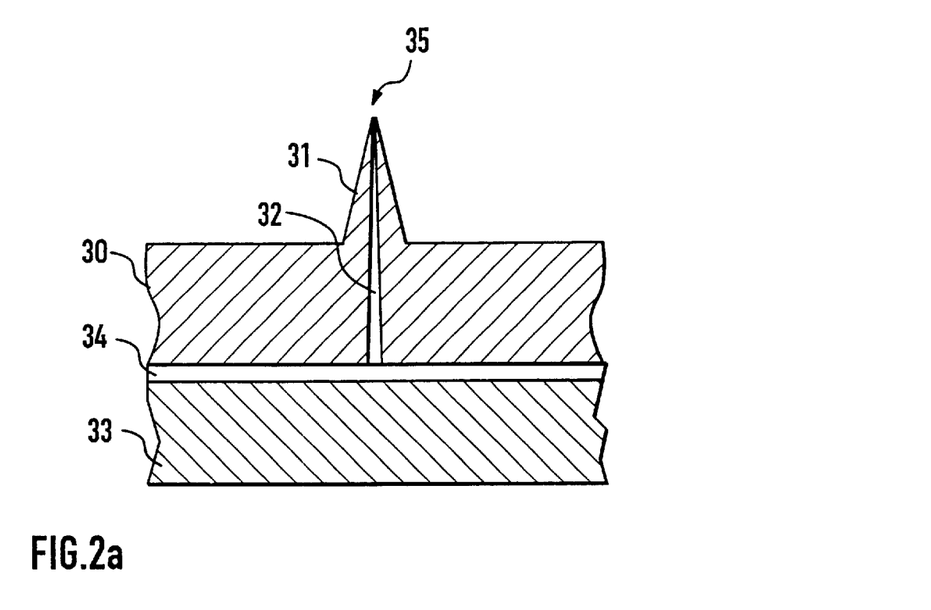
FIG. 2a, b a sectional view of a microchip according to the invention with a micro spray tip (a) and sectional enlargements of this micro spray tip (b)
Figure 2B:
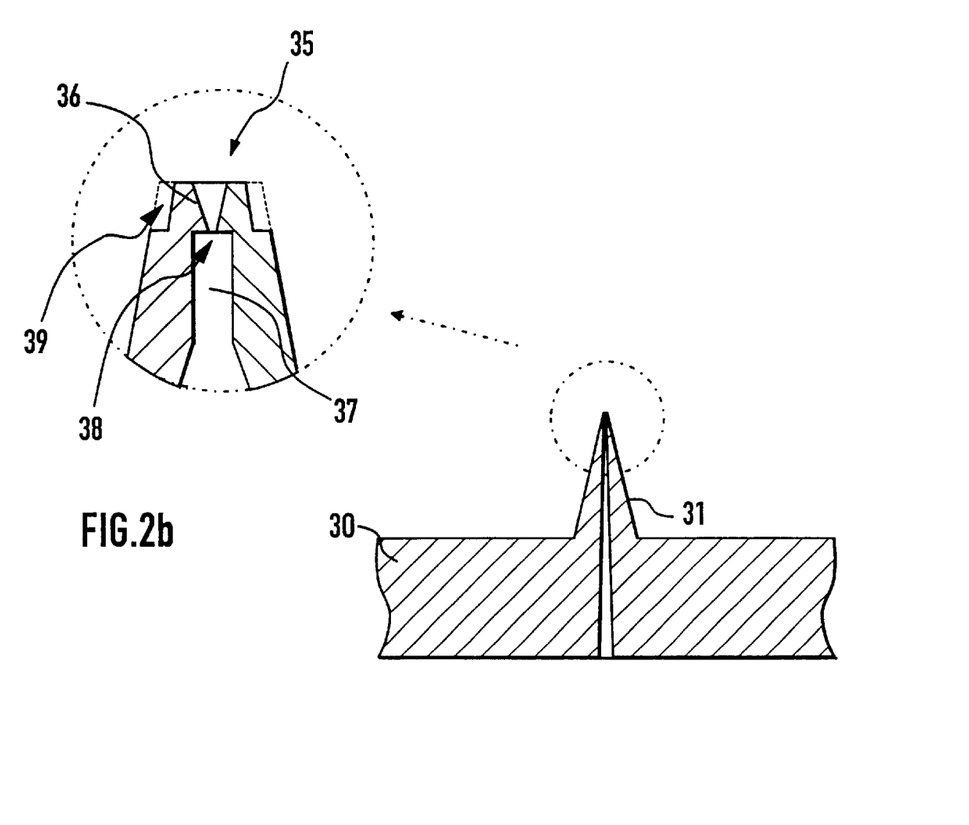

FIGS. 2a and b each show side sectional views of an area of a microchip featuring a micro spray tip according to the invention, whereby FIG. 2b shows a sectional enlargement of the actual micro tip, strengthened in comparison with FIG. 2a.

The microchip features a carrier 30, on which, projecting approximately vertically from the carrier plane, a micro spray tip 31 is arranged. The carrier 30 and the spray tip 31 are designed, according to the invention, as monolithic (single-piece). The spray tip 31 features a passage channel 32, which serves to transport substances to be sprayed from a channel 34 to a spray tip aperture 35. The channel 34 is part of a channel structure, not shown here, which is sealed to the outside by means of a cover plate 33.

FIG. 2b now shows a spray tip 31 according to the invention in greater detail. This features, on sides of the spray aperture 35, first an area 36 which tapers conically inwards. Connected to this area 36 is a drillhole 37 of constant cross-section, whereby an annular internal step arrangement 38 is provided at the transition point between the two areas. The outer diameter of the conically pointed tip 31 is locally reduced 39 in the area of the aperture, in order to bring the spray tip to a finer tip, so as to increase further the electrical fields emerging at the tip and thereby increasing the forces available to take effect on the substances and for the dispersion spraying.

For the parallel or simultaneous examination of a number of substance specimens, it is usual to make use of so-called microtiter plates, referred to as well plates. The specimens to be examined are in this case arranged in matrix fashion in small cavities, known as wells. Such well plates are known, for example, from U.S. Pat. No. 5,457,527, WO 97122754, and WO 95/03538. They consist of a specimen plate or well plate and a base plate, whereby the base plate is made of plastic or glass. Base plate and well plate are connected to one another in such a way that the base plate encloses the wells of the well plate at the bottom.

Figure 3A:
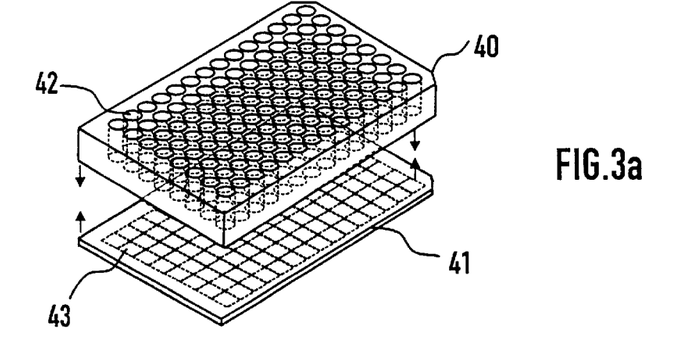
FIG. 3a, b a device according to the invention for the handling of a microchip according to the invention.
Figure 3B:
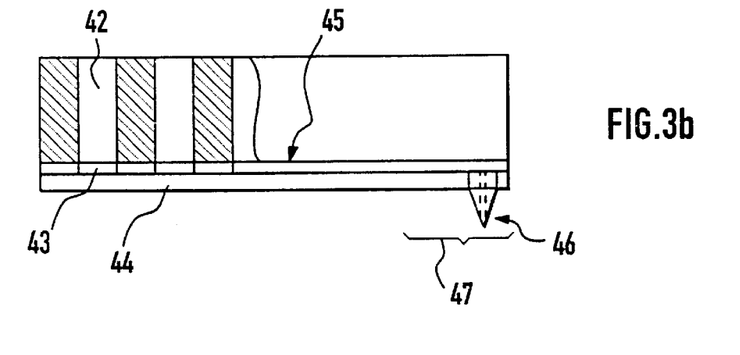

A well plate 40 of this type is shown in perspective in FIG. 3. A microchip 41, likewise shown in perspective, is designed in its external dimensions in such a way that it matches with the well plate 40. The well plate 40 features substance reservoirs or wells 42, in which the substances or reagents required for the individual experiment are accommodated. For the purpose of the conduct of the experiment, these substances are then conveyed by means of specimen delivery apertures 43 to the microchip 41, for example with conventional commercial pipette stations. The spatial arrangement of the wells 42 and the specimen delivery apertures 43 are matched to one another according to the invention in such a way that, once the well plate 40 and the microchip 41 have been brought together, a compact modular unit 40, 41 is formed. Thanks to standardised dimensions, this modular unit can be used without further ado in conventional laboratory or measuring devices. The channel structure 44 of the microchip 41 is located according to the invention on the connection side of the microchip 41 and the well plate 40, while by contrast a micro spray tip 46, also provided for on the microchip 41, is arranged on the opposite side of the microchip 41, and specifically in a peripheral area 47 of the microchip 41. This has the advantage that the spray tip, after the well plate 40 and the microchip 41 have been joined, is to advantage pointed downwards, and is easily accessible from the outside.

Figure 4A:
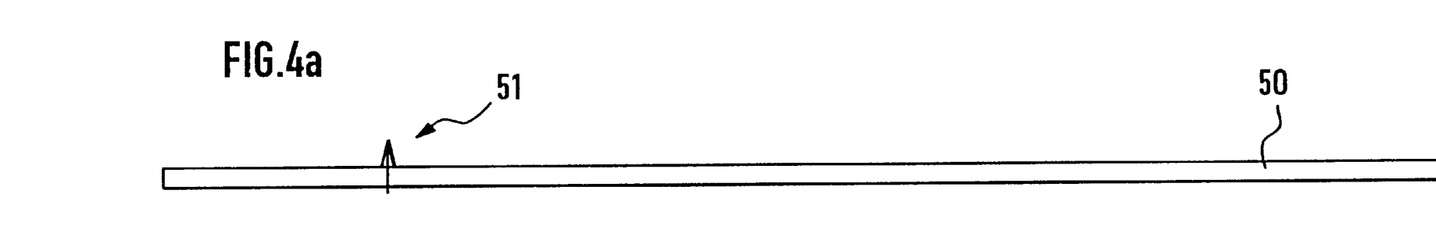
FIG. 4a, b a microfluidic microchip formed lengthways according to the invention, in a schematic side view (a) and rear view (b)
Figure 4B:
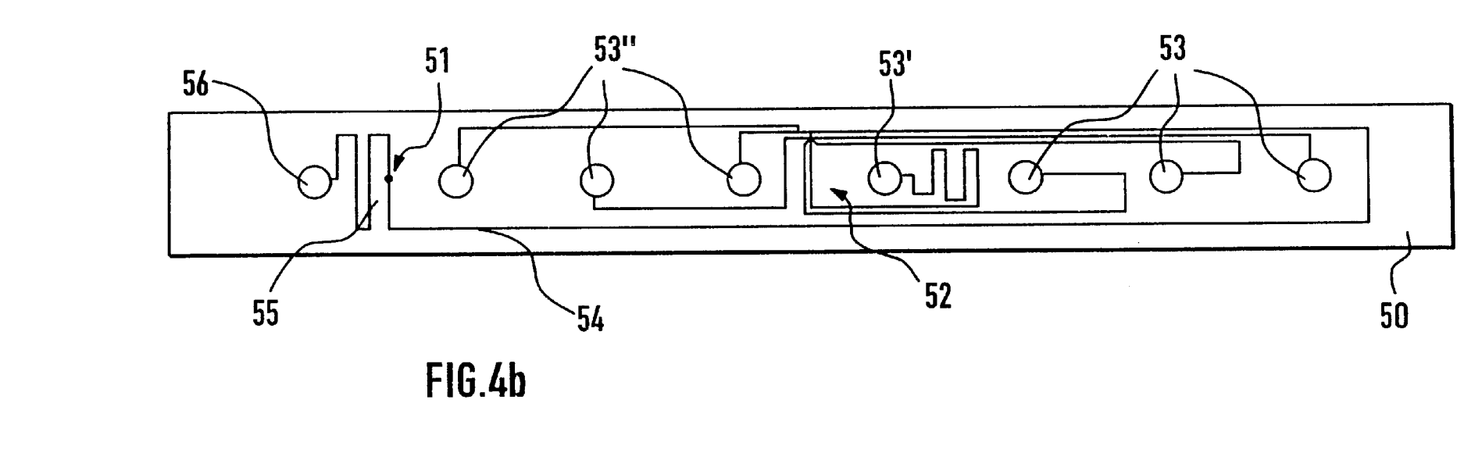

FIG. 4a shows a microfluidic microchip 50 designed longitudinally according to the invention, in a schematic side view. The microchip 50 features, in a peripheral area, a micro spray tip 51. From the side of the microchip 50 shown in FIG. 4b, to the rear and opposite the spray tip, the longitudinal design of the microchip 50 is clear. In the rear view, in addition, the channel structure 52 of the microchip, located on this side, is also visible. The channel structure 52 in this situation features substance delivery channels 53, 53', 53", which open into a separation channel. The separation channel 54 is arranged to advantage in the longitudinal direction of the microchip 50. As a result of this, the effective separation length is maximised, available in particular for the separation of substances. The separation channel opens into a meander-shaped channel area 55, which is located above a connection channel arranged vertically to the plane of the paper, which is in substance-conveying connection with the spray tip 51. A substance sink 56 is then connected to the channel area 55, which serves to accommodate excess substances which are not conducted into the spray tip.

Figure 5:
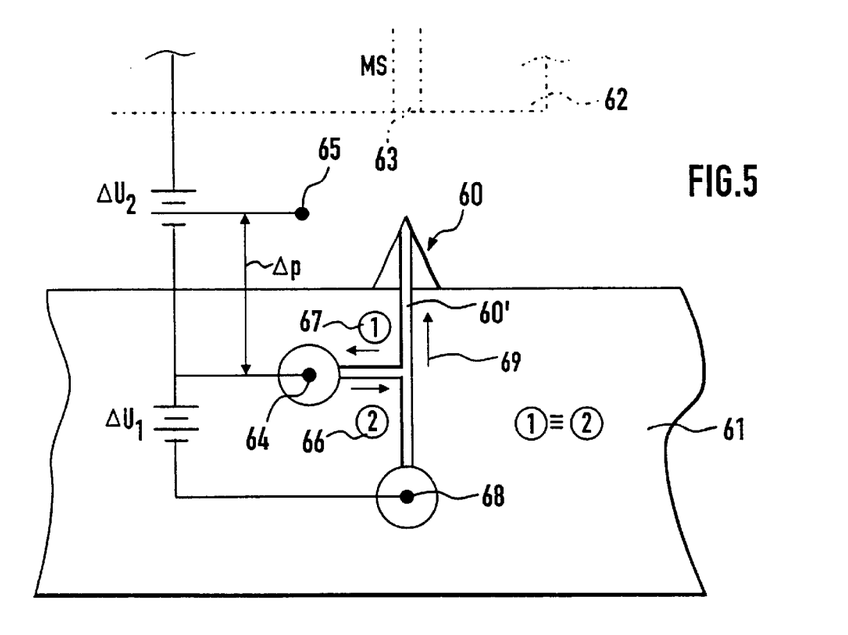
FIG. 5 a schematic representation of a microchip featuring a micro spray tip, to illustrate the potential relationships under a substance flow exerting a hydraulic and electro-osmotic effect.

FIG. 5 shows a schematic representation of a microchip 61 featuring a micro spray tip 60, and serves to illustrate the potential relationships with an overlaid substance flow exerting a hydraulic and electro-osmotic effect. The spray tip 60 in this situation is connected in a substance conveying manner to the microchip 61 by means of a connection channel 60'. Opposite the spray tip 60 a mass spectrometer (MS) 62 is provided for, the aperture 63 of which, as usual, is arranged in the immediate proximity of the spray tip. The dispersion spraying of the substances into the aperture 63 of the MS 62 is effected at normal pressure. Accordingly, normal pressure also pertains at the intake 63 of the MS 62, whereby the ions emerging from the spray tip 60 are automatically drawn into the MS 62, at the normal pressure pertaining, at the intake 63 because of a vacuum pertaining in the interior of the MS 62.

With regard to the gas pressure relationships, a normal pressure pertains at the spray tip 60. Because of the electrical field $\Delta U_1$ imposed between a connection 68 and a liquid junction connection 64, a substance specimen would not migrate to the spray tip 60 but, following the electrical field $\Delta U_1$, would migrate 67 to the connection 64. To prevent this, according to the invention a slight over-pressure $\Delta p$ in relation to normal pressure is imposed at the connection 64, which incurs a hydrodynamic flow 66, 69, which is greater than or equal to the electro-osmotic flow 67, with the result that the substance specimen migrates 69 to the spray tip 60.

Figure 6:
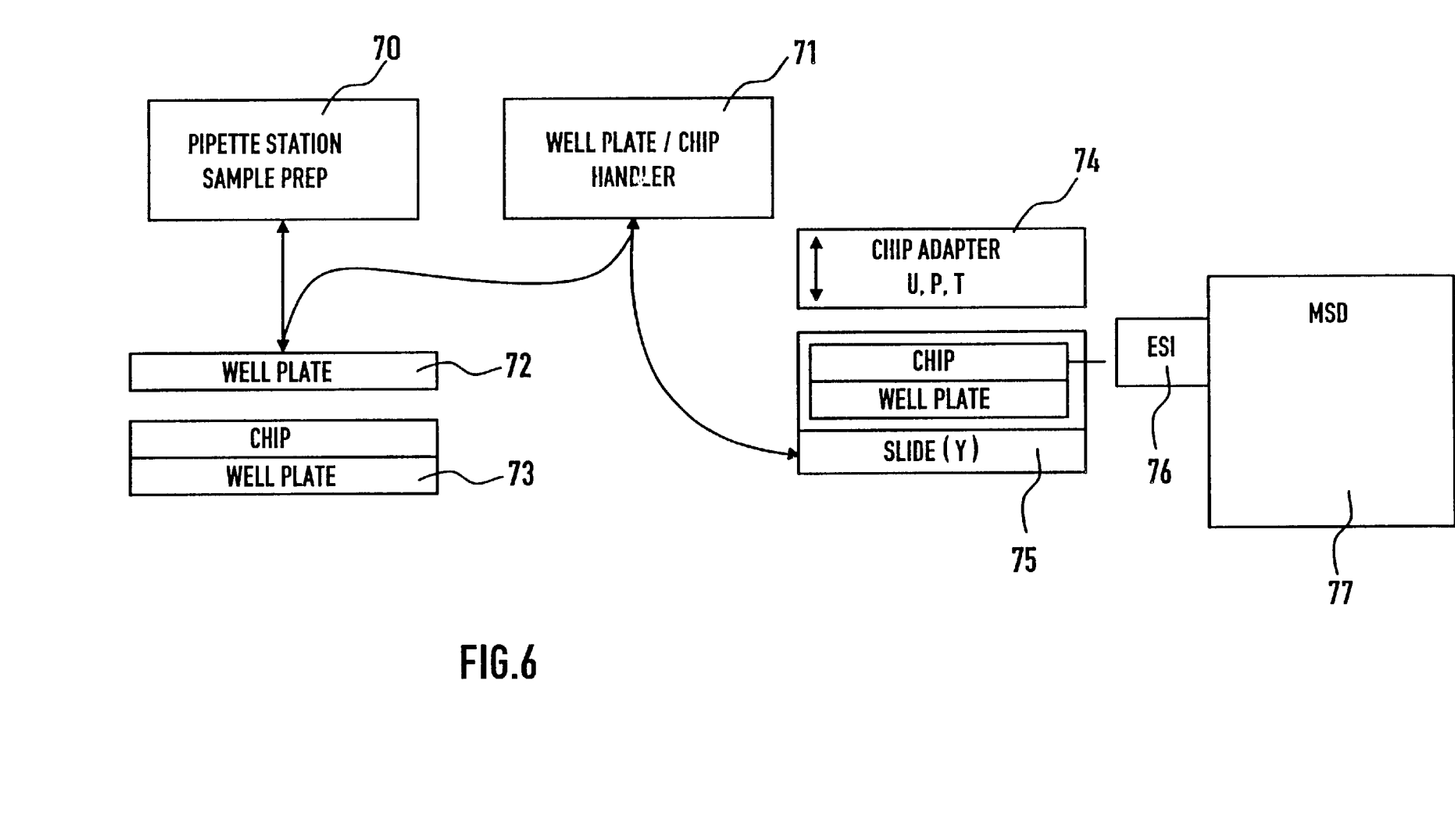
FIG. 6 a working cycle represented in flow diagram form, with the use of the device according to the invention for the handling of a microfluidic microchip featuring a micro spray tip.

Finally, FIG. 6 shows a work cycle with the use of the device according to the invention for the handling of a microfluidic microchip featuring a micro spray tip, and specifically in the form of a flow diagram. Well plates and microchips 73 containing substance specimens are in this case administered in what are referred to as "hotels". From these hotels, the substance specimens 72 in what are known as pipetting stations are conducted to the microchips, after a specimen preparation procedure has been carried out. A robot 71 serves this purpose, which then conveys the microchips to an analysis device, which brings the microchips into contact 74 with an appropriate chemical environment before the analysis which is to be carried out, and only then connects them to the spray chamber 76 of a mass spectrometer 77. By means of a processing mechanism 75, the microchips are moved out of the analysis device and are again made accessible to the robot 71.

I claim:

1. Microfluidic chip for the chemical, physical, and/or biological analysis or synthesis of substances, comprising a channel structure arranged on one side of a carrier having an essentially flat portion, the substances being capable of being moved according to the channel structure under the imposition of an electrical potential, an integrated micro spray tip for dispersion spraying of the substances, the micro spray tip and the carrier being a monolithic single unit;

the micro spray tip and the channel structure being arranged on opposite sides of the same carrier, the micro spray tip including a passage channel projecting substantially at right angles to a plane of the channel structure of the flat portion of the carrier;

the micro spray tip, on the side of the carrier including the channel structure being connected by the passage channel thereof to the channel structure of the carrier flat portion in a substance-conveying manner; and an electrical voltage source connected to the micro spray tip in an electrically-conductive manner for dispersion spraying of the substance.

2. The microfluidic microchip of claim 1 further including a liquid channel connected to the channel structure of the carrier flat portion and the passage channel, the liquid channel being connected to the voltage source and arranged so there is hydrodynamic flow in the passage channel and there are electro-osmotic flow and hydrodynamic flow in the liquid channel, the hydrodynamic flow being at least equal to the electro-osmotic flow.

3. Microfluidic microchip according to claim 1, wherein the micro spray tip and the carrier are made of a polymer material.

4. Microfluidic microchip of claim 3 wherein the polymer is selected from the group consisting essentially of PEEK (polyether etherketone), PI (polyimide), and PMMA (polymethyl metacrylate).

5. Microfluidic microchip according to claim 1, wherein the micro spray tip is connected to a separation channel on the carrier for conveying the chemical, physical, and/or biological analysis or synthesis of the substances.

6. Microfluidic microchip according to claim 1, wherein the micro spray tip is arranged in an outer area of the surface plane of the carrier.

7. Microfluidic microchip according to claim 1 wherein the microchip includes, on the side of the carrier including the channel structure, a cover plate enclosing the channel structure downwards, to provide a substance seal.

8. Microfluidic microchip according to claim 1 wherein the outer diameter of the micro spray tip is between about 10 and 100 $\mu$m, and the height of the micro spray tip is about 1 mm.

9. Microfluidic microchip according to claim 1, wherein the voltage source has a potential for causing matched movement of the substances to one another in such a way that an electro-osmotic substance flow directed towards the micro spray tip is equal to a hydraulic substance flow of the substance towards the spray tip.

10. Microfluidic microchip according to claim 9, further including a source for adjusting the hydraulic substance flow rate between the micro spray tip and the volume outside the microchip.

11. Microfluidic microchip according to claim 10 wherein the source for adjusting includes a variable voltage source.

12. Microfluidic microchip according to claim 10 wherein the source for adjusting includes a variable differential pressure source.

13. Microfluidic microchip according to claim 1, further including an electricity supply for the micro spray tip, the electricity supply including a liquid junction resulting from the substances flowing to the micro spray tip.

14. Microfluidic microchip according to claim 9, wherein a liquid junction where the voltage source is connected to the substances is arranged so a slight liquid overpressure pertains in relation to the pressure prevailing at the micro spray tip.

15. Microfluidic microchip according to claim 14, wherein the liquid junction is arranged so that a liquid overpressure enables an additional liquid to be mixed with the substance being sprayed to the outside volume.

16. The microfluidic microchip of claim 1 wherein the microchip is adapted for use with substances having sufficient electrical conductivity to provide an electrical path through the substances from the voltage source to an exit region of the spray tip, the spray tip being arranged to enable the voltage source to be connected to the exit region only by the substances.

17. The microfluidic microchip of claim 16 wherein walls of the spray tip adapted to contact the substances are electrical insulators.

18. The microfluidic microchip of claim 17 further including a liquid channel connected to the channel structure of the carrier flat portion and the passage channel, the liquid channel being connected to the voltage source and arranged so there is hydrodynamic flow in the passage channel and there are electro-osmotic flow and hydrodynamic flow in the liquid channel, the hydrodynamic flow being at least equal to the electro-osmotic flow.

19. The microfluidic microchip of claim 16 further including a liquid channel connected to the channel structure of the carrier flat portion and the passage channel, the liquid channel being connected to the voltage source and arranged so there is hydrodynamic flow in the passage channel and there are electro-osmotic flow and hydrodynamic flow in the liquid channel, the hydrodynamic flow being at least equal to the electro-osmotic flow.

20. Microfluidic chip for the chemical, physical, and/or biological analysis or synthesis of substances, comprising a channel structure arranged on one side of a carrier having an essentially flat portion, the substances being capable of being moved according to the channel structure under the imposition of an electrical potential, an integrated micro spray tip for dispersion spraying of the substances, the micro spray tip including a passage channel projecting substantially at right angles to a plane of the channel structure of the flat portion of the carrier;

the micro spray tip on the side of the carrier including the channel structure being connected by the passage channel thereof to the channel structure of the carrier flat portion in a substance-conveying manner; and an electrical voltage source connected to the micro spray tip in an electrically-conductive manner for dispersion spraying of the substance, the microchip being adapted for use with substances having sufficient electrical conductivity to provide an electrical path through the substances from the voltage source to an exit region of the spray tip, the spray tip being arranged to enable the voltage source to be connected to the exit region only by the substances.

21. The microfluidic microchip of claim 20 wherein walls of the spray tip adapted to contact the substances are electrical insulators.

22. The microfluidic microchip of claim 21 further including a liquid channel connected to the channel structure of the carrier flat portion and the passage channel, the liquid channel being connected to the voltage source and arranged so there is hydrodynamic flow in the passage channel and there are electro-osmotic flow and hydrodynamic flow in the liquid channel, the hydrodynamic flow being at least equal to the electro-osmotic flow.

23. The microfluidic microchip of claim 20 further including a liquid channel connected to the channel structure of the carrier flat portion and the passage channel, the liquid channel being connected to the voltage source and arranged so there is hydrodynamic flow in the passage channel and there are electro-osmotic flow and hydrodynamic flow in the liquid channel, the hydrodynamic flow being at least equal to the electro-osmotic flow.

* * * * *